US012793825B2

(12) United States Patent
Wang et al.

(10) Patent No.: US 12,793,825 B2
(45) Date of Patent: Nov. 10, 2026

(54) INTELLIGENT VACCINE NEBULIZATION SYSTEM AND METHOD OF USE

(71) Applicant: QINGDAO FUTURE MEDICAL TECHNOLOGY CO., LTD., Qingdao (CN)

(72) Inventors: Qixu Wang, Qingdao (CN); Zhongjin Sun, Qingdao (CN); Weilai Wang, Qingdao (CN)

(73) Assignee: QINGDAO FUTURE MEDICAL TECHNOLOGY CO., LTD., Qingdao (CN)

( * ) Notice: Subject to any disclaimer, the term of this patent is extended or adjusted under 35 U.S.C. 154(b) by 723 days.

(21) Appl. No.: 18/038,980

(22) PCT Filed: Dec. 7, 2021

(86) PCT No.: PCT/CN2021/135893

§ 371 (c)(1),
(2) Date: May 25, 2023

(87) PCT Pub. No.: WO2023/040073

PCT Pub. Date: Mar. 23, 2023

(65) Prior Publication Data

US 2024/0006042 A1 Jan. 4, 2024

(30) Foreign Application Priority Data

Sep. 14, 2021 (CN) ......................... 202111071268.0

(51) Int. Cl.

| | |
|---|---|
| ***G16H 20/13*** | (2018.01) |
| ***A61M 11/00*** | (2006.01) |
| ***G16H 40/67*** | (2018.01) |

(52) U.S. Cl.

CPC ............. *G16H 20/13* (2018.01); *A61M 11/00* (2013.01); *G16H 40/67* (2018.01); *A61M 2205/6063* (2013.01)

(58) Field of Classification Search

CPC ........ G16H 20/10; G16H 20/13; G16H 10/60; G16H 40/67; G16H 20/40; G16H 20/17;

(Continued)

(56) References Cited

U.S. PATENT DOCUMENTS 5,692,640 A * 12/1997 Caulfield ............... G16H 20/10
221/199
6,571,790 B1 * 6/2003 Weinstein ................. A61J 1/00
128/200.14

(Continued)

*Primary Examiner* — Victoria Murphy

(74) *Attorney, Agent, or Firm* — Jiwen Chen; Joywin IP Law PLLC

(57) ABSTRACT

The present invention provides an intelligent vaccine nebulization system and a use method, and the system is characterized in that the system comprises an intelligent vaccine nebulization device, a mist storage tank and a cloud server; the intelligent vaccine nebulization device comprises a main cabinet, an intelligent main control module and a plurality of functional modules provided on the main cabinet, wherein the functional modules include an identity information input module, a vaccine information input module, a temporary vaccine storage module, a dosing transfer module, an aerosol output module, a mist storage tank management module, a human-computer interaction module and a communication port, in which the intelligent main control module is respectively connected with the functional modules and the intelligent main control module is communicated with the cloud server. And strict and accurate vaccination and management are ensured. It is controlled by the intelligent main control module, and through steps of identity information and vaccine information input, vaccine temporary storage, dosing transfer, aerosol output, mist storage tank management (Continued)

and the like, vaccination and vaccinator information could be stored in the cloud server and have access to, so that nebulization vaccination is realized.

18 Claims, 8 Drawing Sheets

(58) Field of Classification Search
CPC .......... A61M 15/0086; A61M 2202/30; A61M 2205/6009; A61M 11/00; A61M 2205/6063; A61M 2205/505; A61M 2205/3553; A61M 2205/6072
See application file for complete search history.

(56) References Cited

U.S. PATENT DOCUMENTS

| | | | | |
|---|---|---|---|---|
| 2003/0221687 | A1* | 12/2003 | Kaigler | A61M 15/00 128/200.14 |
| 2004/0260700 | A1* | 12/2004 | Wang | G06Q 10/10 |
| 2009/0076650 | A1* | 3/2009 | Faes | G07F 11/42 700/231 |
| 2011/0238432 | A1* | 9/2011 | DeLoach | G16H 40/20 705/2 |
| 2014/0322682 | A1* | 10/2014 | Baym | G09B 5/02 340/5.6 |
| 2018/0308569 | A1* | 10/2018 | Luellen | G16H 20/10 |
| 2021/0030979 | A1* | 2/2021 | Zimlich, Jr. | G16H 40/67 |
| 2022/0016365 | A1* | 1/2022 | Power | A61M 15/0086 |
| 2022/0148701 | A1* | 5/2022 | Cipollone | G16H 40/67 |

* cited by examiner

INTELLIGENT VACCINE NEBULIZATION SYSTEM AND METHOD OF USE

This is a U.S. national stage application of PCT Application No. PCT/CN2021/135893 under 35 U.S.C. 371, filed Dec. 7, 2021 in Chinese, claiming priority of Chinese Application No. 202111071268.0, filed Sep. 14, 2021, all of which are hereby incorporated by reference.

TECHNICAL FIELD

The present invention belongs to the technical field of intelligent system for vaccination, and also relates to the technical field of medical information processing and the technical field of communication, and is specifically to an intelligent vaccine nebulization system and a method of use thereof.

BACKGROUND TECHNOLOGY

A large number of studies of vaccines show that: for infectious diseases that infect body through respiratory mucosa, partial vaccination is more effective and safer than peripheral vaccination. Partial vaccination, such as inhaled aerosol COVID-19 vaccine, has fought the defense against virus at mucosal membrane, and could avoid blood-borne infections caused by bacteria contamination upon the opening of injection needles.

The inhaled aerosol COVID-19 vaccine is effective because it could activate mucosal immunity of body. Mucosal immunity is related to globulin A (IgA) and this immunoglobulin could be obtained from breast milk at birth and begins to produce automatically as grown up with its distribution in breast milk, saliva and mucosal secretions on gastrointestinal tract, respiratory tract and genito-urinary tract, which is the first line of defense to prevent the invasion of pathogens.

The inhaled aerosol COVID-19 vaccine could activate the production of IgA: the inhaled vaccine transports the antigen to the nasopharyngeal associated lymphoid tissue (NALT) and presents the antigen to the cell (APC), and then presents it to T cells, which can then activate IgA+B cell development. After antigen-specific CD4+ cells and IgA+B cells migrate to the upper respiratory tract through the thoracic duct and blood circulation, IgA+B cells differentiate into IgA+plasma cells under the action of the cytokines secreted by CD4+ cells to produce IgA dimers. It then binds to the polymerized Ig receptors existing on the epithelial mucosal cells to become secreted IgA, which is finally released to the upper respiratory tract surface to play a protective role.

At the Pujiang Innovation Forum on Jun. 3, 2021, Chen Wei, a researcher of the Academy of Military Sciences, who is also an academician of the Chinese Academy of Engineering, stated that an adenovirus vector inhaled aerosol COVID-19 vaccine developed by her team is applying for emergency use. This means that in the future, the COVID-19 vaccine could be vaccinated in a non-injection manner by only inhaling the atomized vaccine and holding breath for a few seconds.

Compared with the injection vaccine, the advantages of inhaled aerosol COVID-19 vaccine are obvious, which includes:

1. The dose is small, which is about only one-fifth compared with that of the injection route, no vaccine bottle is required, this solves a problem called 'locking' in the manufacture of vaccine bottles, and transportation requirements of vaccine is correspondingly reduced.
2. The production capacity is increased because vaccine dose is reduced to only one-fifth of traditional injection vaccine; in another word, the reduction in single dosage means a significant increase in production capacity.
3. The immune effect is good, the injection vaccine could only produce two types of immunity: humoral immunity+cellular immunity, but the inhaled aerosol vaccine could produce three types of immunity: humoral immunity+cellular immunity+mucosal immunity and the protection effect is better.
4. The immune response is fast. After the nebulization vaccine being inhaled, it could quickly take effect in nasal, throat, trachea, alveoli and mucous membranes.
5. The population of immunization is much easier. Compared with injection, inhaled vaccine is less painful. It is much more suitable for people who are 'fear of needles' or 'need phobia', and more likely to be accepted by children.

SUMMARY OF THE INVENTION

However, the standard process of the inhaled aerosol COVID-19 vaccine requires a nurse to accurately take out an appropriate amount of vaccine from vaccine container by a pipette and drop it into the nebulizer, and then the nurse or vaccinator activates the nebulizer. the process requires obviously a lot of manual participation and control, which is low in efficiency and long in vaccination period, and further causing the turnover rate of the nebulizer is far from satisfaction and the possibility of error is high. It could not fulfill the needs of large-scale, short-term and high-efficiency vaccination, such as the inhaled aerosol COVID-19 vaccine.

Therefore, how to design an intelligent vaccine nebulization system and method of use to realize automatic, efficient and convenient inhaled aerosol COVID-19 vaccination has become an urgent take in the prevention of COVID-19 and it is also an urgent problem in the technical field.

In order to solve the above-mentioned problems in the prior art, the present invention provides an intelligent vaccine nebulization system and a method of use, which can realize automatic, efficient and convenient nebulization vaccination.

The object of the present invention is achieved through the following technical solutions.

An intelligent vaccine nebulization system comprising: an intelligent vaccine nebulization device, a mist storage tank and a cloud server, wherein the intelligent vaccine nebulization device includes a main cabinet, an intelligent main control module and a plurality of functional modules provided on the main cabinet, wherein the functional modules include an identity information input module, a vaccine information input module, a temporary vaccine storage module, a dosing transfer module, an aerosol output module, a mist storage tank management module, a human-computer interaction module and a communication port, in which the intelligent main control module is respectively connected with the functional modules and the intelligent main control module is communicated with the cloud server;

wherein, the identity information input module is configured to receive ID information of vaccinator and send to the cloud server through the intelligent main control module;

- the vaccine information input module is configured to recognize vaccine manufacturers, vaccine types and production batch numbers and supports user settings or downloading vaccine storage parameters, nebulization parameters and usage guidelines from the cloud server according to the recognized vaccine types;
- the temporary vaccine storage module is configured to adapt to vaccine containers by different vaccine manufacturers to provide suitable storage conditions for vaccine and ensure the effectiveness of vaccine during the entire vaccination process;
- the dosing transfer module is configured to automatically and accurately extract specified dose of vaccine and to deliver the measured amount of vaccine to the aerosol output module according to dosage requirements of vaccines;
- the aerosol output module is configured to automatically perform vaccine nebulization according to nebulization guidelines of vaccines, which is provided with an aerosol outlet through which aerosol is filled into the mist storage tank;
- the mist storage tank management module is configured to perform detection and to install the mist storage tank before nebulization and to distribute the mist storage tank in which vaccine after nebulization by the aerosol output module is filled into to vaccinator for inhalation, in which the installation of the mist storage tank is to connect the mist storage tank to the aerosol outlet of the aerosol output module and the detection before nebulization is to check whether the mist storage tank is inserted into the aerosol outlet and is in place;
- the human-computer interaction module is configured to display vaccination information and a human-machine interface and to send reminders to working staff and vaccinator;
- the communication port is configured to connect to communicable devices;
- the intelligent main control module is configured to control the functional modules of the intelligent vaccine nebulization system to upload or download the information and record of vaccinator and nebulization related information and record, and to execute programs to complete a whole process including vaccine storage, nebulization and mist storage tank output according to vaccinator information and vaccine information;
- the mist storage tank is a container for storing vaccine aerosol, which is connected to the aerosol output module to receive the vaccine aerosol produced which is inhaled by vaccinator for vaccination;
- the cloud server is configured to interact with the intelligent main control module to access vaccination information, vaccine information and vaccinator information; and
- the main cabinet is configured to accommodate the functional modules and used to receive and store the vaccines and the mist storage tank and to output the mist storage tank.

As an improvement, the intelligent vaccine nebulization system further includes an inhalation quality detection module configured to detect whether a vaccination process is normally run according to preset vaccination quality requirements; if not, an inhalation quality detection module is configured to generate notifications for manual intervention or to activate preset operations automatically.

As a further improvement, the inhalation quality detection module includes a detection camera or/and a working process detection sensor device; wherein the working process detection sensor device includes an installation detection sensor, a photoelectric sensor, a body posture sensor and an air pressure sensor, which is configured to detect whether the inhalation posture and the volume inhaled by vaccinator meet the preset vaccination requirements and provide feedbacks through the human-machine interface on the human-computer interaction module and to determine whether a vaccination process is finished on the basis of inhalation detected and give feedbacks on the human-machine interface on the human-computer interaction module; and vaccinator is guided by the human-machine interface of the human-computer interaction module to put the working process detection sensor device back in place.

As a further improvement, the intelligent vaccine nebulization system further includes a disposable mist storage tank recovery device configured to recover and treat medical wastes, and vaccinator is guided by the human-machine interface of the human-computer interaction module to put used mist storage tank to designated recycling place.

As a further improvement, the disposable mist storage tank recovery device includes a waste recovery processing chamber, a mist storage tank recovery opening and a mist storage tank recovery chamber door; the mist storage tank management module includes a mist storage tank management chamber and a mist storage tank management chamber door; the aerosol output module includes a mist generation device, a mist storage tank output device and a mist storage tank extraction outlet; and the vaccine temporary storage module includes a vaccine storage chamber, a vaccine storage chamber door, a vaccine temporary storage rack and a controllable low-temperature refrigeration device configured to maintain vaccines in a low-temperature environment; the controllable low-temperature refrigeration device is further configured to maintain the temperature of the dosing transfer module and the aerosol output module.

As a further improvement, the main cabinet includes a shell, wherein the communication port, the human-computer interaction module, the mist storage tank management chamber door, the mist storage tank extraction outlet, the mist storage tank recovery opening, the vaccine storage chamber door and the identity information input module are disposed on the shell.

As a further improvement, the human-computer interaction module includes a display module and an audio guide module; the display module is configured to display vaccination information and the human-machine interface, and the audio guide module is configured to generate guiding or warning sounds to working staff or vaccinator; the camera device includes a detection camera and a detection camera display and the detection camera and the detection camera display are provided on a top part of the shell of the main cabinet.

As a further improvement, the dosing transfer module includes a vaccine information scanner, a pipetting needle, a program-controlled dosing pump and a three-dimensional moving device, wherein the vaccine information scanner is arranged in the vaccine storage chamber, the pipetting needle is connected to the program-controlled dosing pump and the program-controlled dosing pump is provided on the three-dimensional moving device; the program-controlled dosing pump and the three-dimensional moving device are controlled by the intelligent main control module.

As a further improvement, the mist storage tank includes a one-way valve, a tank body and a cover; wherein the one-way valve is the portion where the mist storage tank connected to the aerosol output module; once the mist storage tank is unplugged from the aerosol output module, the one-way valve ensures that the aerosol locked in the mist storage tank and not lost; when the user opens the cover to inhale the aerosol in the mist storage tank, airflow enters into the mist storage tank through the one-way valve, which is convenient for vaccinator to inhale the aerosol in the mist storage tank.

A method of using the intelligent vaccine nebulization system comprises:

Step 1: reading ID information of vaccinator, connecting to the cloud server, retrieving personal health information, vaccine type and vaccination requirements to determine whether the vaccination is allowed;

Step 2: controlling the dosing transfer module to automatically and accurately extract required dosage of vaccine according to dosage requirement of vaccine nebulization;

Step 3: controlling the mist storage tank management module to detect whether the mist storage tank is installed in place; if usage requirements are not met, the mist storage tank is automatically installed or replaced;

Step 4: controlling the aerosol output module to automatically complete vaccine nebulization and fill it into the mist storage tank according to parameters of nebulizer provided by vaccine manufactures and vaccine nebulization;

Step 5: forwarding the mist storage tank and reminding vaccinator to take away the mist storage tank from the mist storage tank extraction outlet through the human-computer interaction module and guide vaccinator to complete vaccine inhalation;

Step 6: generating a vaccination record of vaccine nebulization and saving it on the cloud server.

As a further improvement, performing a step 5A after the step 5, wherein the step 5A including: controlling the inhalation quality detection module to detect whether a vaccination process is normally run according to preset vaccination quality requirements; if not, generating notifications for manual intervention or activating preset operations.

As a further improvement, performing a step 5B after the step 5A, wherein the step 5B including: controlling the disposable mist storage tank recovery device to open the mist storage tank recovery opening; guiding vaccinator to put used mist storage tank to the mist storage tank recovery opening by the human-machine interface of the human-machine interaction module; starting medical waste procedures when it is detected that the mist storage tank is put in.

As a further improvement, the step 1 further includes an automatic recognition and storage procedure including: S1: obtaining a vaccine code; S2: retrieving vaccine storage parameters, nebulization parameters and usage guidelines; S3: detecting whether vaccines are put in; S4:starting executing vaccine storage program, and automatically setting storage environment conditions according to according to the vaccine storage parameters, nebulization parameters and usage guidelines.

As a further improvement, in the step 1, conditions for the determination whether the vaccination is allowed include: whether the age is within an allowed vaccination range, whether they belong to a group who should not get a vaccine, whether they belong to a group who should delay vaccination and whether the vaccination record is matched with vaccines disposed in the intelligent vaccine nebulization system; if the vaccination is allowed, entering into the next step, otherwise exit.

Beneficial Results:

Compared with the prior art, the present invention has many advantages and positive effects: the present invention relates to an intelligent vaccine nebulization system and a method of use and its advantages are to realize an automatic vaccination process of nebulization vaccine to minimize manual intervention, improve utilization rate and turnover rate of nebulizer; the vaccination process is standardized, the quality is controllable, and the entire vaccination process could be traced. Specific advantages and positive effects include:

1. The vaccination registration is automated. It could automatically determine whether vaccinator meets vaccination requirements and vaccine type should be vaccinated according to personal information of vaccinator.
2. The automation and standardization of vaccine storage is realized. The present invention could automatically set and provide a suitable vaccine storage environment according to vaccine storage related parameters, such as temperature, humidity, production date, shelf life and the like, it also could automatically check the validity period of vaccines regularly and give warnings when expired vaccines detected.
3. The automatic precise vaccine nebulization is realized. The present invention could extract specified doses of vaccine for nebulization automatically and accurately according to preset dose requirements of vaccine nebulization.
4. An automatic efficient distribution of vaccine aerosol is realized. By proposing brand-new mist storage tank, the utilization rate and turnover rate of nebulizer are maximized, and on the other hand and cross-infection caused by vaccine nebulizer is effectively prevented. The disinfection and maintenance cost for the nebulizer is saved.
5. An intelligent inhalation quality detection ensures standardization of vaccine nebulization, the vaccination quality is under control to guarantee the effect of vaccination.
6. The mist storage tank could be automatically recovered and disinfected, effectively avoid secondary pollution in the process of vaccination, protecting environment and reducing workload for medical staff.
7. The whole process of nebulization vaccination could be automatically recorded to ensure that the whole process of vaccination could be traced. The information is uploaded and stored in the cloud server to ensure that vaccinator could receive consistent, standardized and high-quality vaccination on each intelligent vaccine nebulization system at any time.
8. The automation of a whole process of vaccination from registration to medical waste recycling is realized. Manual intervention is minimized, the efficiency and vaccination quality is improved, the workload of medical staff is reduced and medical cost is saved, and mistakes caused by manual operation could be avoided.

The present invention could improve the popularity of vaccination. The whole process of operation does not require manual intervention and could be deployed on any occasion.

Figure 1:
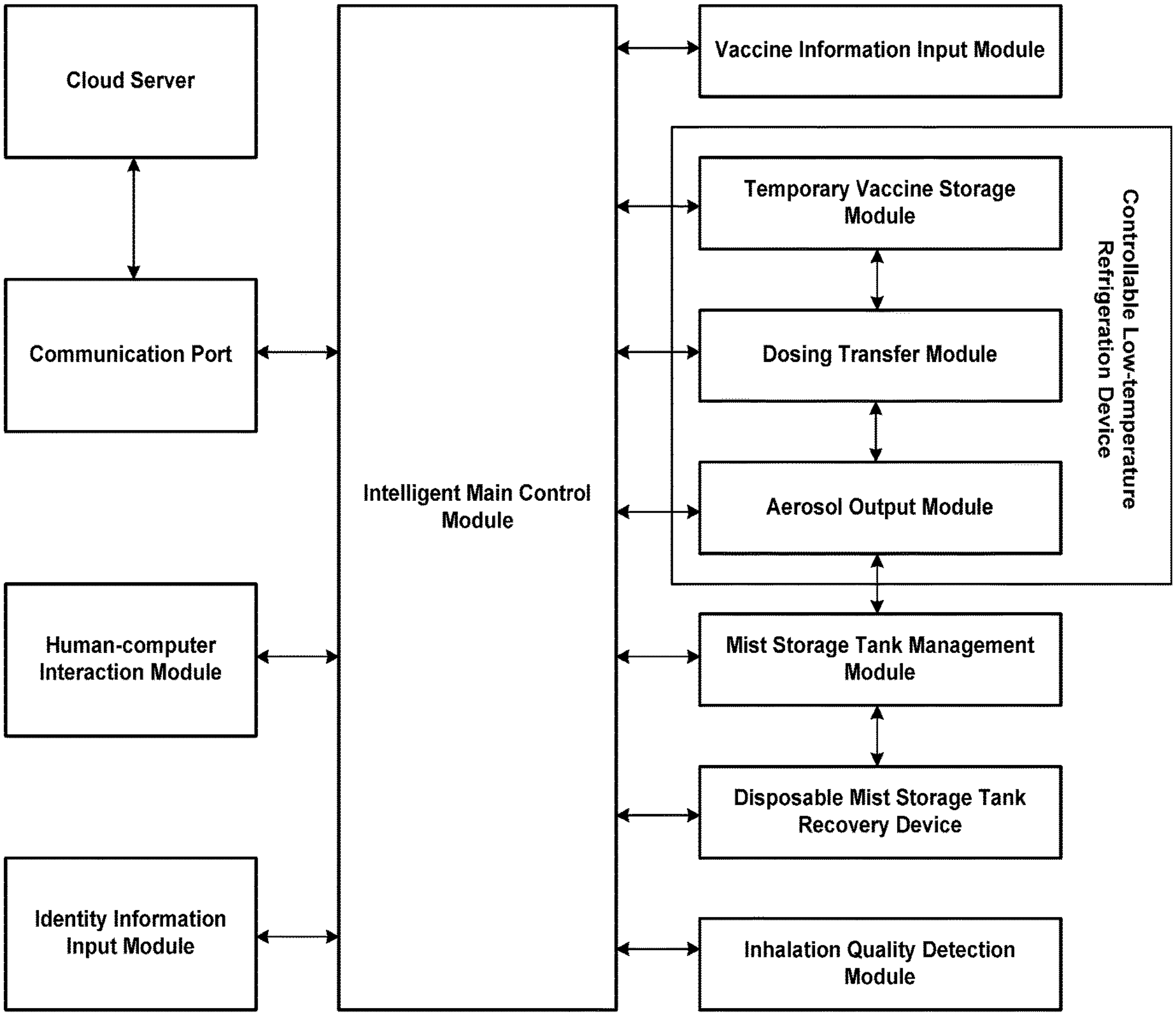
FIG. 1 is a logical functional block diagram of an intelligent vaccine nebulization system according to one aspect of the present invention.

In the figures, 1—temporary vaccine storage module, 1.1—vaccine temporary storage rack, 1.2—vaccine information scanner, 1.3—vaccine bottle, 1.4—pipette needle, 1.5—program-controlled dosing pump, 1.6—X rail, 1.7—Y rail, 1.8—Z rail, 2—communication port, 3—mist storage tank management module, 3.1—mist storage tank management chamber door, 3.2—mist storage tank management door handle, 4—disposable mist storage tank recovery device, 4.1—mist storage tank recovery opening, 4.2—mist storage tank recovery chamber door handle, 4.3—mist storage tank recovery chamber door, 5—detection camera, 6—detection camera display, 7—display module, 8—audio guide module, 9—mist storage tank extraction outlet, 10—identity information input module, 11—mist storage tank, 11.1—one-way valve, 11.2—tank body, 11.3—cover, 12—working process detection sensor device, 13—horizontal push device, 13.1—clamp locking device, 13.2—automatic clamp plate device, 14. vertical lifting device.

DETAILED DESCRIPTION OF THE INVENTION

The present invention will be further described in detail below with reference to the accompanying drawings and embodiments.

An intelligent vaccine nebulization system provided by the present invention is show in FIG. 1 to FIG. 10, which includes an intelligent vaccine nebulization device, a mist storage tank 11 and a cloud server. The intelligent vaccine nebulization device includes a main cabinet, an intelligent main control module and a plurality of functional modules provided on the main cabinet, wherein the functional modules include an identity information input module 10, a vaccine information input module, a temporary vaccine storage module, a dosing transfer module, an aerosol output module, a mist storage tank management module, a human-computer interaction module and a communication port 2. The intelligent main control module is respectively connected with the functional modules and the intelligent main control module is communicated with the cloud server.

Each functional module is described in detail as follows.

The identity information input module 10 is configured to receive ID information of vaccinator and send to the cloud server through the intelligent main control module for verification, or even receiving recommendations from available vaccine manufactures and vaccine type according to their age and health records.

The vaccine information input module is configured to recognize vaccine manufacturers, vaccine types and production batch numbers, and supports user settings or downloading vaccine storage parameters, nebulization parameters and usage guidelines according to the recognized vaccine types from the cloud server.

The temporary vaccine storage module 1 is configured to adapt to vaccine containers by different vaccine manufacturers to provide suitable storage conditions for vaccine and ensure the effectiveness of vaccine during the entire vaccination process.

The dosing transfer module is configured to automatically and accurately extract specified dose of vaccine and to deliver the measured amount of vaccine to the aerosol output module according to dosage requirements of vaccines.

The aerosol output module is configured to automatically perform vaccine nebulization according to nebulization guidelines of vaccines, which is provided with an aerosol outlet through which aerosol is filled into the mist storage tank.

The mist storage tank management module 3 is configured to perform detection and to install the mist storage tank 11 before nebulization, and then to distribute the mist storage tank 11 in which vaccine after nebulization by the aerosol output module is filled into to vaccinator for inhalation. The installation of the mist storage tank 11 is to connect the mist storage tank 11 to the aerosol outlet of the aerosol output module and the detection before nebulization is to check whether the mist storage tank 11 is inserted into the aerosol outlet and is in place.

The human-computer interaction module is configured to display vaccination information and a human-machine interface, and to send reminders to working staff and vaccinator.

The communication port 2 is configured to connect to communicable devices, which can perform uplink communications or downlink communications.

The intelligent main control module is configured to control the functional modules of the intelligent vaccine nebulization system to upload or download the information and record of vaccinator and nebulization related information and record, and to execute programs to complete a whole process including vaccine storage, nebulization and mist storage tank output according to vaccinator information and vaccine information.

The mist storage tank 11 is a container for storing vaccine aerosol, which is connected to the aerosol output module to receive the vaccine aerosol produced. The vaccine aerosol is inhaled by vaccinator for vaccination.

The cloud server is configured to interact with the intelligent main control module to access vaccination information, vaccine information and vaccinator information, which is selectively networked with national or local disease control centers for data interaction.

The main cabinet is configured to accommodate the functional modules and used to receive and store the vaccines and the mist storage tank 11 and to output the mist storage tank 11.

Further the intelligent vaccine nebulization system includes an inhalation quality detection module, which is configured to detect whether a vaccination process is normally run according to preset vaccination quality requirements. If not, the inhalation quality detection module automatically generates notifications for manual intervention or activates preset operations.

Figure 4:
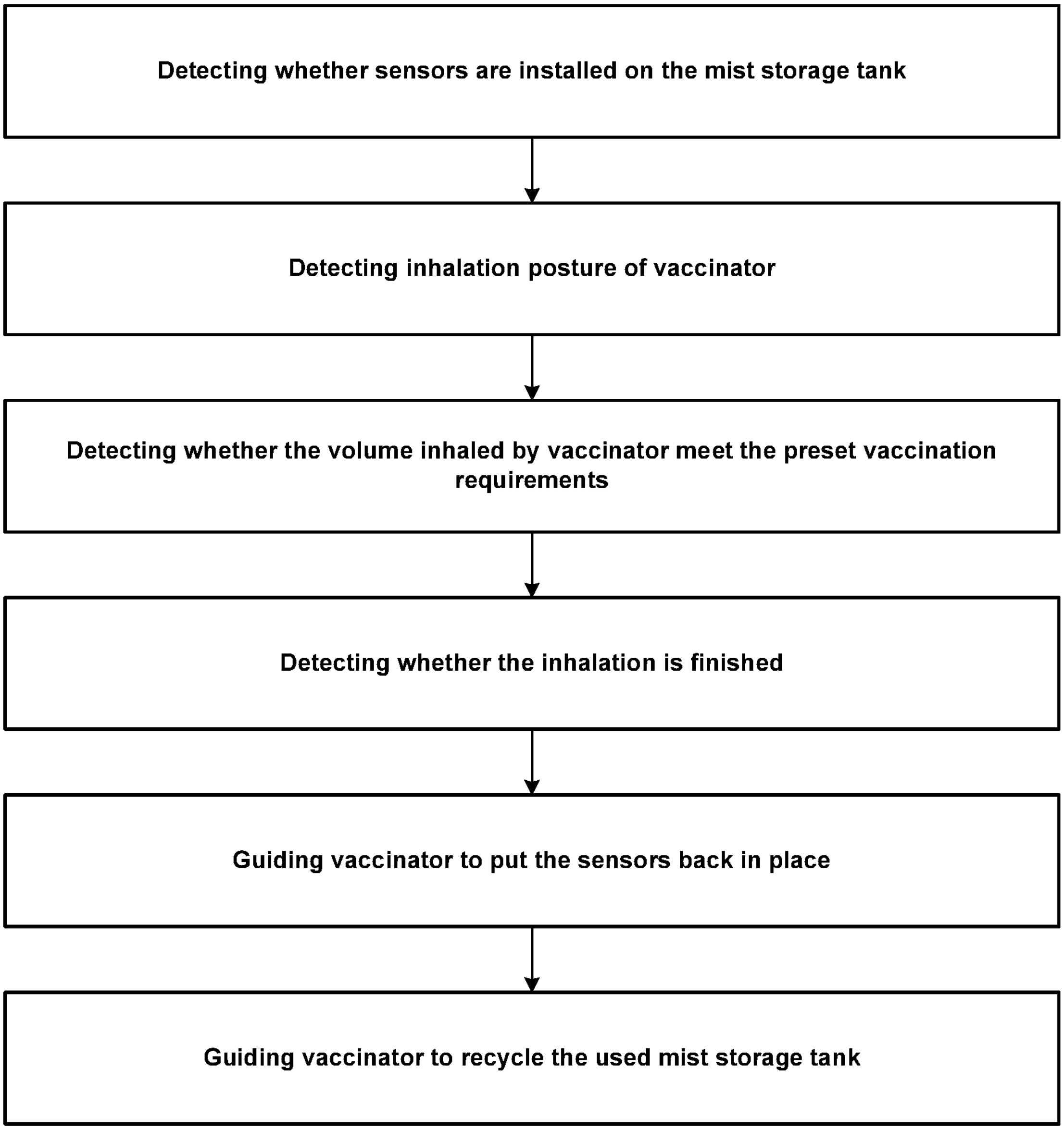
FIG. 4 is a block diagram of a workflow of a quality detection module in the intelligent vaccine nebulization system according to one aspect of the present invention.
Figure 7:
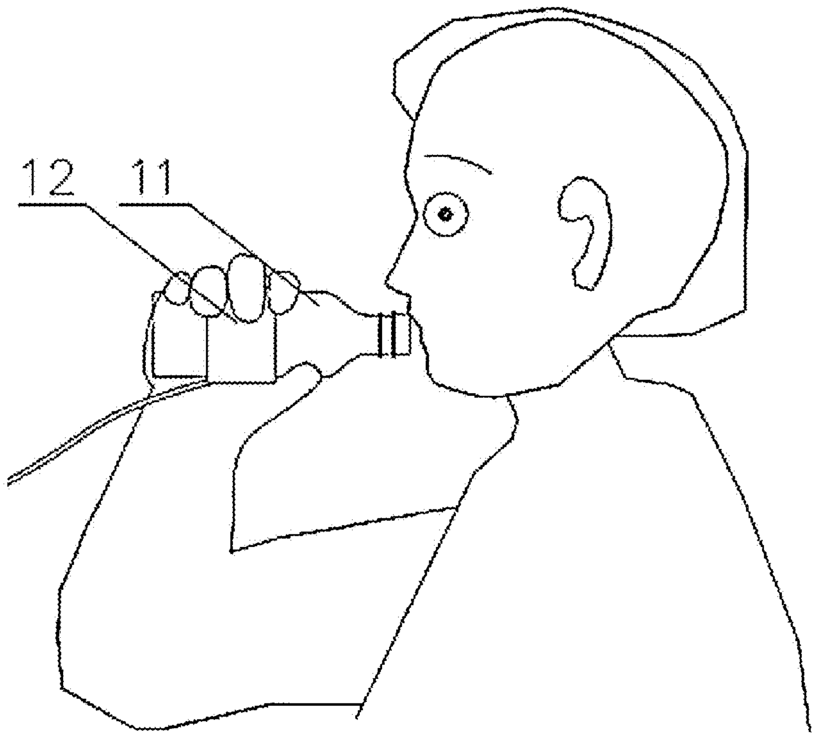
FIG. 7 shows a working state of an inhalation quality detection module in the intelligent vaccine nebulization system according to one aspect of the present invention.
Figure 9:
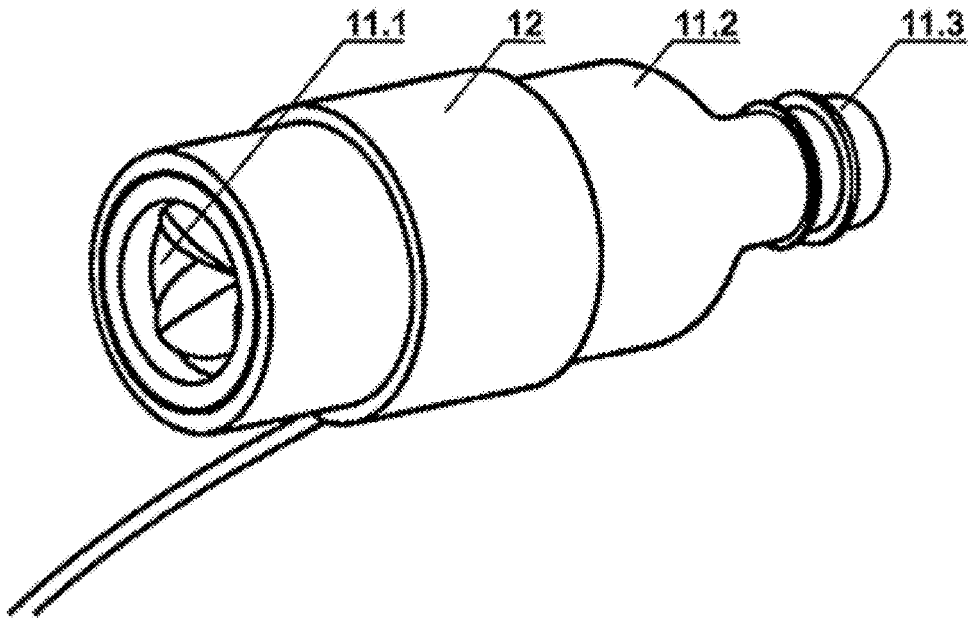
FIG. 9 shows a state of the intelligent vaccine nebulization system according to one aspect of the present invention in which the mist storage tank is being detected by a working process detection sensor device.

Furthermore, as shown in FIG. 4, FIG. 7 and FIG. 9, the inhalation quality detection module includes a detection camera or/and a working process detection sensor device 12. The working process detection sensor device 12 includes an installation detection sensor, a photoelectric sensor, a body posture sensor and an air pressure sensor, which is configured to detect whether the inhalation posture and the volume inhaled by vaccinator meet the preset vaccination requirements and provide feedbacks through the human-machine interface on the human-computer interaction module and to determine whether a vaccination process is finished on the basis of inhalation detected and give feedbacks on the human-machine interface on the human-computer interaction module; and then vaccinator is guided by the human-machine interface of the human-computer interaction module to put the working process detection sensor device 12 back in place. The working process detection sensor device 12 is sleeved on the mist storage tank 11 in usage.

Figure 5:
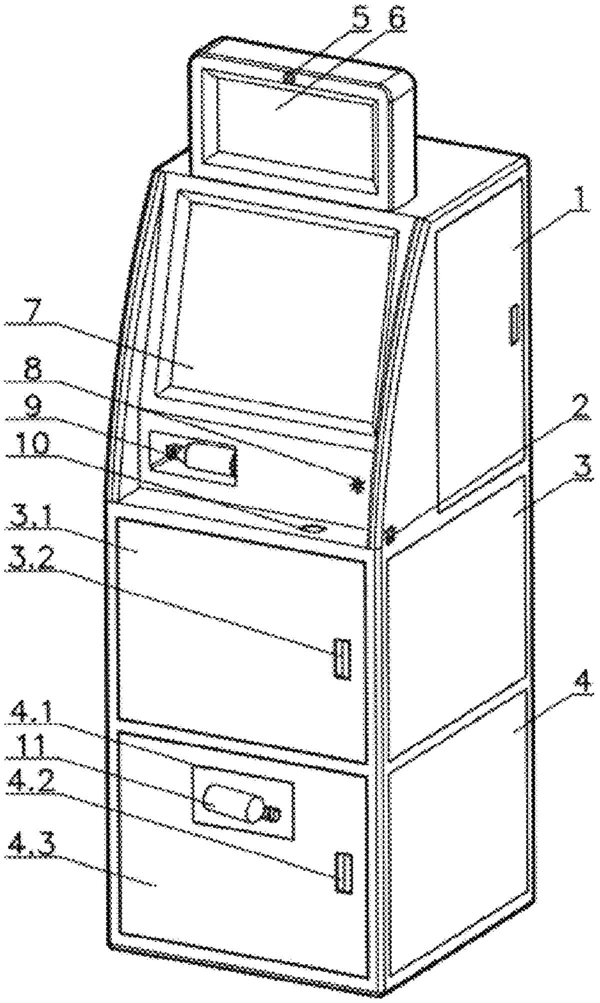
FIG. 5 is a perspective view of a main cabinet in the intelligent vaccine nebulization system according to one aspect of the present invention.

As shown in FIG. 5, the intelligent vaccine nebulization system further includes a disposable mist storage tank recovery device 4 configured to recover and treat medical wastes. Vaccinator is guided by the human-machine interface of the human-computer interaction module to put used mist storage tank 11 to designated recycling place.

To be specific, as shown in FIG. 5, the disposable mist storage tank recovery device 4 includes a waste recovery processing chamber, a mist storage tank recovery opening 4.1 and a mist storage tank recovery chamber door 4.3; wherein the mist storage tank recovery chamber door 4.3 may also be provided with a mist storage tank recovery chamber door handle 4.2. The mist storage tank management module 3 includes a mist storage tank management chamber and a mist storage tank management chamber door 3.1; wherein the mist storage tank management chamber door 3.1 may also be provided with a mist storage tank management chamber door handle 3.2.

As shown in FIG. 1 and FIG. 5, the aerosol output module includes a mist generation device, a mist storage tank output device and a mist storage tank extraction outlet 9.

Figure 6:
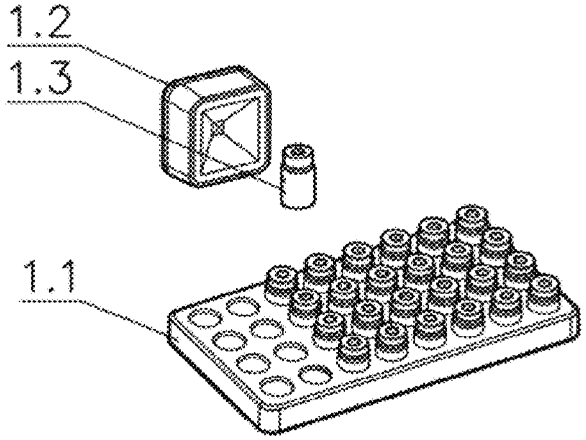
FIG. 6 is a schematic diagram of a vaccine information input module in the intelligent vaccine nebulization system according to one aspect of the present invention.

As shown in FIG. 5 and FIG. 6, the vaccine temporary storage module 1 includes a vaccine storage chamber, a vaccine storage chamber door, a vaccine temporary storage rack 1.1 and a controllable low-temperature refrigeration device configured to maintain vaccines in a low-temperature environment. Further, the controllable low-temperature refrigeration device is also configured to maintain the temperature of the dosing transfer module and the aerosol output module.

As shown in FIG. 5, the main cabinet includes a shell. The communication port 2, the human-computer interaction module, the mist storage tank management chamber door 3.1, the mist storage tank extraction outlet 9, the mist storage tank recovery opening 4.1, the vaccine storage chamber door and the identity information input module are disposed on the shell.

As shown in FIG. 5, the human-computer interaction module includes a display module 7 and an audio guide module 8; the display module 7 is configured to display vaccination information and the human-machine interface, and the audio guide module 8 is configured to generate guiding or warning sounds to working staff or vaccinator. The display module 7 and the audio guide module 8 are provided on a front part of the shell of the main cabinet. The camera device includes a detection camera 5 and a detection camera display 6, and the detection camera 5 and the detection camera display 6 are provided on a top part of the shell of the main cabinet.

Figure 10:
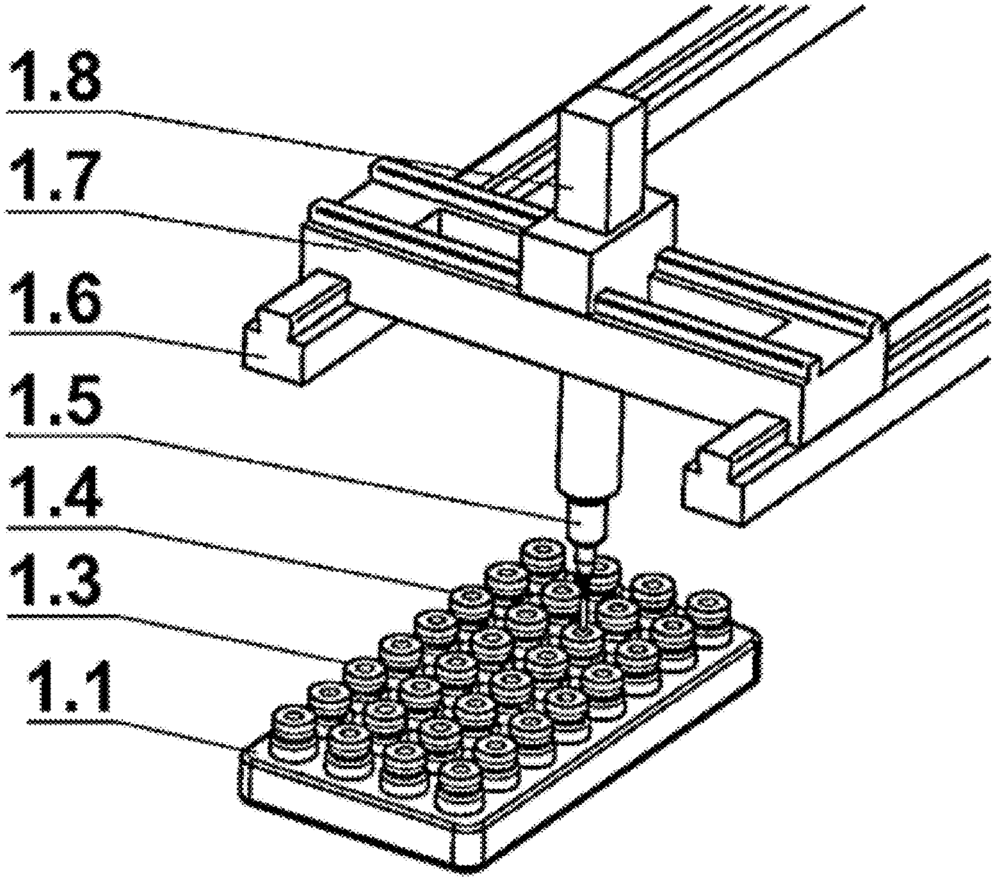
FIG. 10 is a schematic structural diagram of a vaccine quantitative removal module in the intelligent vaccine nebulization system according to one aspect of the present invention.

As shown in FIG. 6 and FIG. 10, the dosing transfer module includes a vaccine information scanner 1.2, a pipetting needle 1.4, a program-controlled dosing pump 1.5 and a three-dimensional moving device. The vaccine information scanner 1.2 is arranged in the vaccine storage chamber. The pipetting needle 1.4 is connected to the program-controlled dosing pump 1.5 and the program-controlled dosing pump 1.5 is provided on the three-dimensional moving device. Both of the program-controlled dosing pump 1.5 and the three-dimensional moving device are controlled by the intelligent main control module. The three-dimensional moving device is composed of an X rail 1.6, a Y rail 1.7 and a Z rail 1.8, which could drive the pipette needle 1.4 and the program-controlled dosing pump 1.5 to move in the three-dimensional space, to quickly pinpoint the required vaccine bottle 1.3 to aspirate the vaccine.

Figure 8:
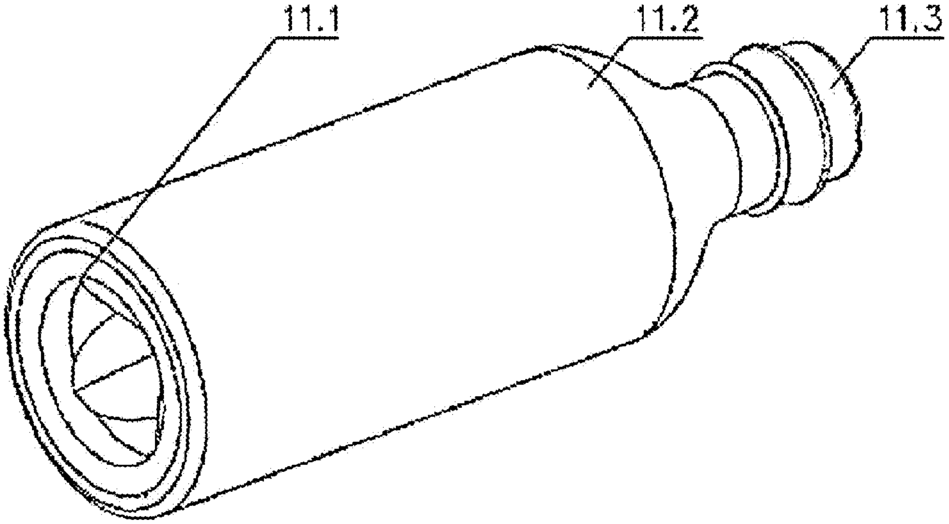
FIG. 8 is a perspective view of an mist storage tank used in the intelligent vaccine nebulization system according to one aspect of the present invention.

As shown in FIG. 8, the mist storage tank 11 includes a one-way valve 11.1, a tank body 11.2 and a cover 11.3; wherein the one-way valve 11.1 is also the portion where the mist storage tank 11 connected to the aerosol output module. Once the mist storage tank 11 is unplugged from the aerosol output module, the one-way valve 11.1 could ensure the aerosol locked in the mist storage tank 11 and not lost; when the user opens the cover 11.3 to inhale the aerosol in the mist storage tank 11, airflow enters into the mist storage tank 11 through the one-way valve 11.1, which is convenient for vaccinator to inhale the aerosol in the mist storage tank 11.

Figure 11:
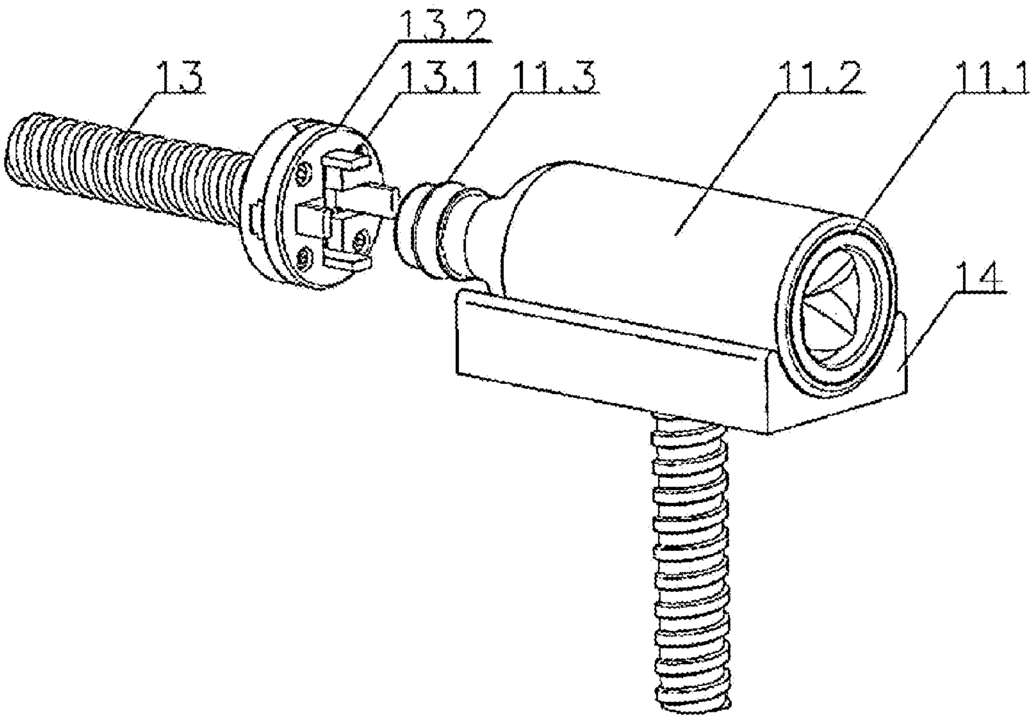
FIG. 11 is a schematic diagram of an automatic filling and taking structure for the mist storage tank in the intelligent vaccine nebulization system according to one aspect of the present invention.

As shown in FIG. 11, a mist storage tank delivery structure includes of the mist storage tank management module 3 includes a horizontal push device 13 and a vertical lifting device 14. The horizontal push device 13 includes a clamp locking device 13.1 and an automatic clamp plate device 13.2.

The vertical lifting device 14 lifts the mist storage tank 11 to the aerosol outlet of the aerosol output module, the one-way valve 11.1 of the mist storage tank 11 is aligned with the aerosol outlet, the horizontal push device 13 pushes the mist storage tank 11 to move laterally to insert it into the aerosol outlet to realize the automatic installation of the mist storage tank 11. When the aerosol being fully filled, claws of the automatic clamp plate device 13.2 automatically clamp the cover 11.3 of the mist storage tank 11; when the horizontal push device 13 pulls the mist storage tank 11 to separate from the aerosol output, claws of the automatic clamp plate device 13.2 loosen the mist storage tank 11 to realize an automatic separation of the mist storage tank 11 and the mist storage tank 11 falls into the mist storage tank extraction outlet 9.

A pressure sensor or a light sensor is installed at the aerosol outlet of the aerosol output module, which is used to detect whether the mist storage tank 11 is inserted into the aerosol outlet and whether the mist storage tank 11 is in place. The mist storage tank management module 3 connects to the pressure sensor and the light sensor to perform the detection before nebulization.

Figure 2:
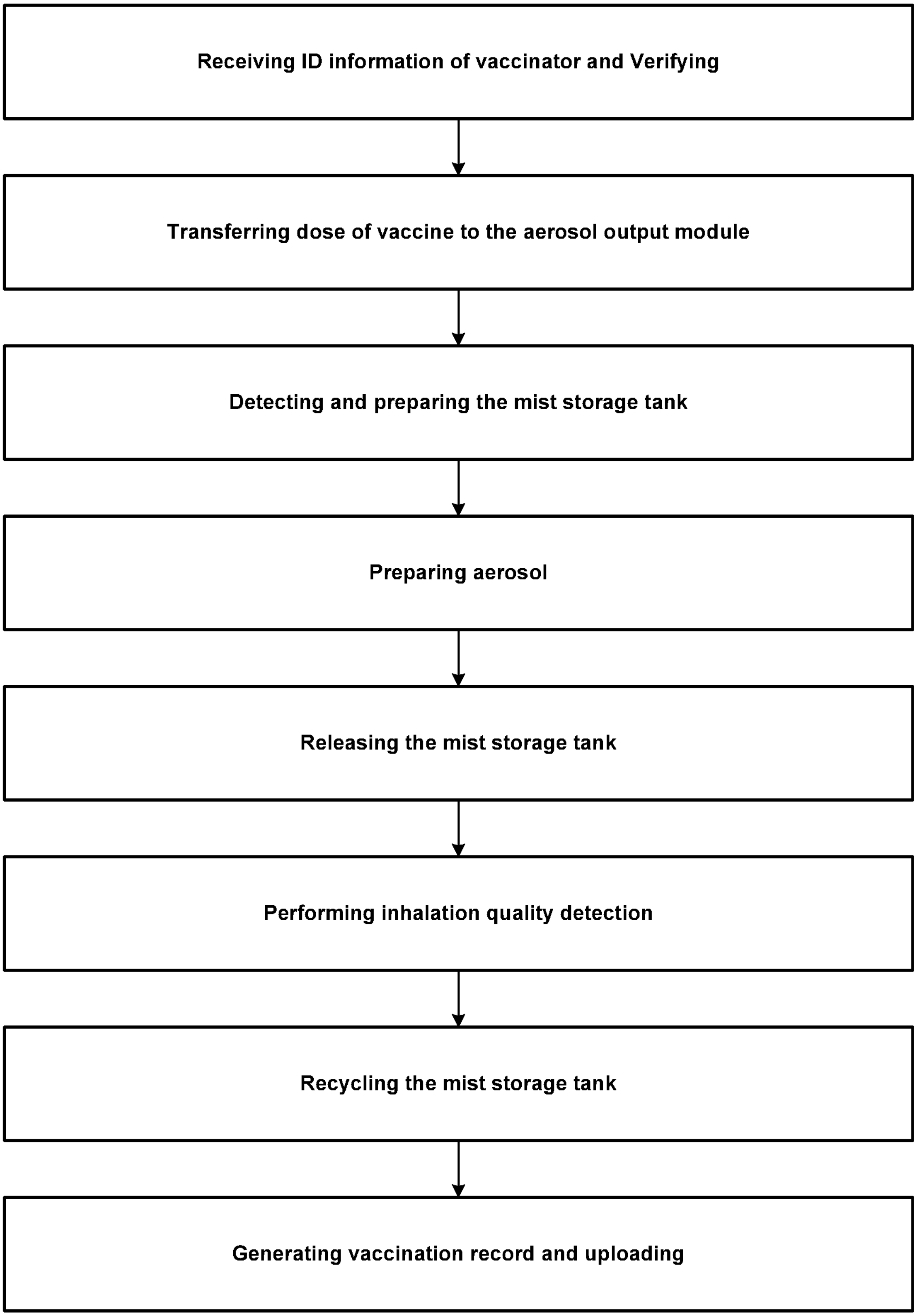
FIG. 2 is a flow chart of a method for using the intelligent vaccine nebulization system according to one aspect of the present invention.

Referring to FIG. 2, a method for using the intelligent vaccine nebulization system including the following steps:

Step 1: Reading ID information of vaccinator, connecting to the cloud server, retrieving personal health information, vaccine type and vaccination requirements to determine whether the vaccination is allowed;

Step 2: Controlling the dosing transfer module to automatically and accurately extract required dosage of vaccine according to dosage requirement of vaccine nebulization;

Step 3: Controlling the mist storage tank management module to detect whether the mist storage tank 11 is installed in place; if usage requirements are not met, the mist storage tank is automatically installed or replaced;

Step 4: Controlling the aerosol output module to automatically complete vaccine nebulization and fill it into the mist storage tank 11 according to parameters of nebulizer provided by vaccine manufactures and vaccine nebulization;

Step 5: Forwarding the mist storage tank 11 and reminding vaccinator to take away the mist storage tank 11 from the mist storage tank extraction outlet 9 through the human-computer interaction module and guide vaccinator to complete vaccine inhalation;

Step 6: Generating a vaccination record of vaccine nebulization and saving it on the cloud server;

Furthermore, a step 5A is performed after the step 5. The step 5A includes: controlling the inhalation quality detection module to detect whether a vaccination process is normally run according to preset vaccination quality requirements; if not, generating notifications for manual intervention or activating preset operations. The specific procedures are shown in FIG. 4.

Furthermore, a step 5B is performed after the step 5A. The step 5B includes: controlling the disposable mist storage tank recovery device 4 to open the mist storage tank recovery opening 4.1; guiding vaccinator to put used mist storage tank 11 to the mist storage tank recovery opening 4.1 by the human-machine interface of the human-machine interaction module; starting medical waste procedures, such as disinfection, crushing and the like when it is detected that the mist storage tank 11 is put in.

Figure 3:
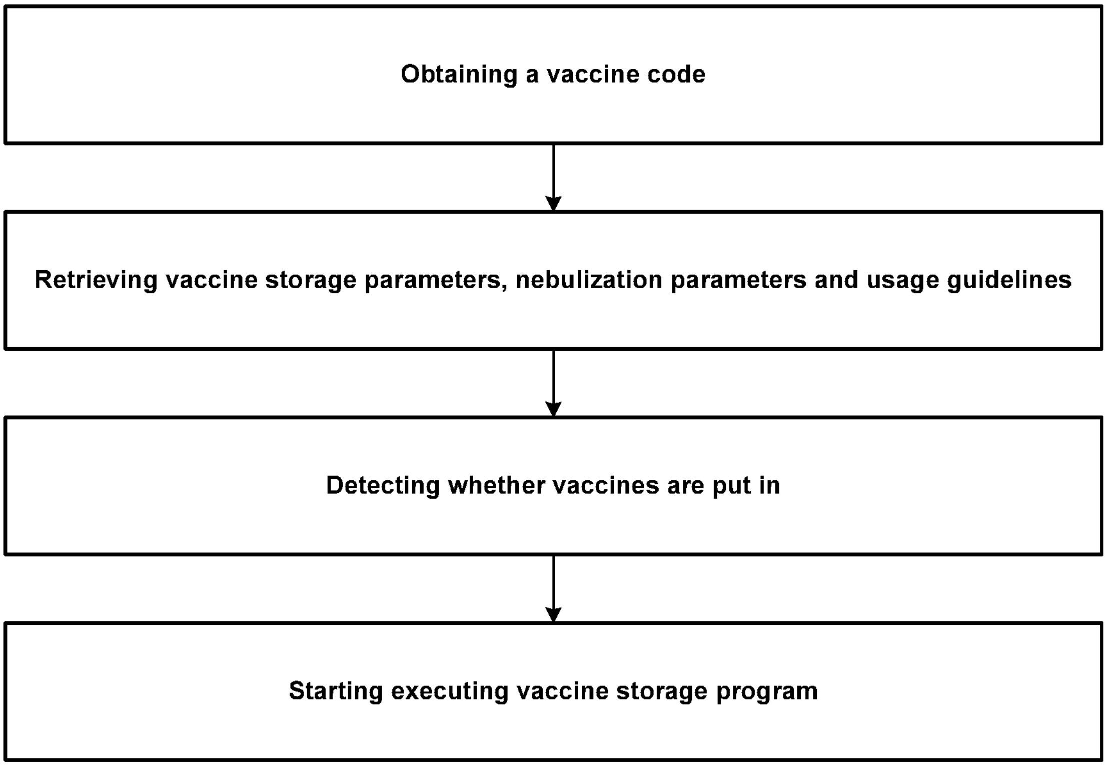
FIG. 3 is a block diagram of a workflow of a vaccine information input module in the intelligent vaccine nebulization system according to one aspect of the present invention.

Furthermore, referring to FIG. 3, the step 1 also includes an automatic recognition and storage procedure including: S1: obtaining a vaccine code; S2: retrieving vaccine storage parameters, nebulization parameters and usage guidelines; S3: detecting whether vaccines are put in; S4:starting executing vaccine storage program, and automatically setting storage environment conditions according to according to the vaccine storage parameters, nebulization parameters and usage guidelines. It could regularly check the validity period of vaccines and generate warnings for expired doses to take preset treatment measures.

Preferably, in the step 1, conditions for the determination whether the vaccination is allowed include: whether the age is within an allowed vaccination range, whether they belong to a group who should not get a vaccine, whether they belong to a group who should delay vaccination and whether the vaccination record is matched with vaccines disposed in the intelligent vaccine nebulization system. If the vaccination is allowed, entering into the next step, otherwise exit.

The above are only the preferred embodiments of the present invention, and are not intended to limit the present invention in other forms. Any person familiar with the profession may use the technical content disclosed above to change or modify the equivalent of equivalent changes. Examples. However, any simple modifications, equivalent changes and modifications made to the above embodiments based on the technical essence of the present invention without departing from the content of the technical solution of the present invention still belong to the protection scope of the technical solution of the present invention.

What is claimed is:

1. An intelligent vaccine nebulization system comprising: an intelligent vaccine nebulization device, a mist storage tank and a cloud server, wherein the intelligent vaccine nebulization device comprises a main cabinet, an intelligent main control module and a plurality of functional modules provided on the main cabinet, wherein the plurality of functional modules include an identity information input module, a vaccine information input module, a temporary vaccine storage module, a dosing transfer module, an aerosol output module, a mist storage tank management module, a human-computer interaction module and a communication port; wherein: the intelligent main control module is respectively connected with the plurality of functional modules and the intelligent main control module is communicated with the cloud server;

the identity information input module is configured to receive ID information of vaccinator and send the ID information of the vaccinator to the cloud server through the intelligent main control module;

the vaccine information input module is configured to recognize vaccine manufacturers, vaccine types and production batch numbers and supports user settings or downloading vaccine storage parameters, nebulization parameters and usage guidelines from the cloud server according to the recognized vaccine types;

the temporary vaccine storage module is configured to adapt to vaccine containers by different vaccine manufacturers to provide suitable storage conditions for the vaccine containers and to ensure an effectiveness of a vaccine within the vaccine containers during an entire vaccination process;

the dosing transfer module is configured to automatically and accurately extract a specified dose of the vaccine and to deliver the specified dose of the vaccine to the aerosol output module according to dosage requirements of the vaccine;

the aerosol output module is configured to automatically perform vaccine nebulization according to nebulization guidelines of the vaccine, the aerosol output module is provided with an aerosol outlet through which aerosol is filled into the mist storage tank;

the mist storage tank management module is configured to perform detection before nebulization and to install the mist storage tank before nebulization and to distribute the aerosol from the mist storage tank to the vaccinator for inhalation, wherein the installation of the mist storage tank is to connect the mist storage tank to the aerosol outlet of the aerosol output module and the detection before nebulization is to check whether the mist storage tank is inserted into the aerosol outlet and is in place;

the human-computer interaction module is configured to display vaccination record and a human-machine interface and to send reminders to working staff and the vaccinator;

the communication port is configured to connect to communicable devices;

the intelligent main control module is configured to control the plurality of functional modules of the intelligent vaccine nebulization system to upload or download the ID information of the vaccinator and the nebulization parameters and usage guidelines, and to execute programs to complete a whole process including vaccine storage, nebulization and mist storage tank output according to the ID information of the vaccinator and information on the vaccine manufacturers, the vaccine types and the production batch numbers;

the mist storage tank is a container for storing vaccine aerosol, which is connected to the aerosol output module to receive the vaccine aerosol produced which is inhaled by the vaccinator for vaccination;

the cloud server is configured to interact with the intelligent main control module to access the vaccination record, the information on the vaccine manufacturers, the vaccine types and the production batch numbers, and the ID information of the vaccinator; and the main cabinet is configured to accommodate the plurality of functional modules and used to receive and store the vaccines and the mist storage tank and to dispense the mist storage tank.

2. The intelligent vaccine nebulization system according to claim 1, further comprising an inhalation quality detection module configured to detect whether a vaccination process is normally run according to preset vaccination quality requirements; if not, the inhalation quality detection module is configured to generate notifications for manual intervention or to activate preset operations automatically.

3. The intelligent vaccine nebulization system according to claim 1, further comprising a disposable mist storage tank recovery device configured to recover and treat medical wastes, and the human-machine interface of the human-computer interaction module is configured to guide the vaccinator to put a used mist storage tank to a designated recycling place.

4. The intelligent vaccine nebulization system according to claim 3, wherein the disposable mist storage tank recovery device comprises a waste recovery processing chamber, a mist storage tank recovery opening and a mist storage tank recovery chamber door; the mist storage tank management module comprises a mist storage tank management chamber and a mist storage tank management chamber door; the aerosol output module comprises a mist generation device, a mist storage tank output device and a mist storage tank extraction outlet; and the temporary vaccine storage module comprises a vaccine storage chamber, a vaccine storage chamber door, a vaccine temporary storage rack and a controllable low-temperature refrigeration device configured to maintain vaccines in a low-temperature environment; the controllable low-temperature refrigeration device is further configured to maintain a temperature of the dosing transfer module and the aerosol output module.

5. The intelligent vaccine nebulization system according to claim 4, wherein the main cabinet comprises a shell, wherein the communication port, the human-computer interaction module, the mist storage tank management chamber door, the mist storage tank extraction outlet, the mist storage tank recovery opening, the vaccine storage chamber door and the identity information input module are disposed on the shell.

6. The intelligent vaccine nebulization system according to claim 2, wherein the inhalation quality detection module further comprises a camera device; and wherein the human-computer interaction module comprises a display module and an audio guide module; the display module is configured to display the vaccination record and the human-machine interface, and the audio guide module is configured to generate guiding or warning sounds to working staff or the vaccinator; the camera device comprises a detection camera and a detection camera display and the detection camera and the detection camera display are provided on a top part of a shell of the main cabinet.

7. The intelligent vaccine nebulization system according to claim 4, wherein the dosing transfer module comprises a vaccine information scanner, a pipetting needle, a program-controlled dosing pump and a three-dimensional moving device, wherein the vaccine information scanner is arranged in the vaccine storage chamber, the pipetting needle is connected to the program-controlled dosing pump and the program-controlled dosing pump is provided on the three-dimensional moving device; the program-controlled dosing pump and the three-dimensional moving device are controlled by the intelligent main control module.

8. The intelligent vaccine nebulization system according to claim 1, wherein the mist storage tank comprises a one-way valve, a tank body and a cover; wherein the one-way valve is located where the mist storage tank connects to the aerosol output module.

9. A method of using the intelligent vaccine nebulization system according to claim 1, comprising:

Step 1: reading the ID information of the vaccinator, connecting to the cloud server, retrieving personal health information, vaccine type and vaccination requirements to determine whether the vaccination is allowed;

Step 2: controlling the dosing transfer module to automatically and accurately extract the specified dose of the vaccine according to dosage requirement of vaccine nebulization;

Step 3: controlling the mist storage tank management module to detect whether the mist storage tank is installed in place; if usage requirements are not met, the mist storage tank is automatically installed or replaced;

Step 4: controlling the aerosol output module to automatically complete vaccine nebulization and fill the aerosol into the mist storage tank according to parameters of a nebulizer;

Step 5: forwarding the mist storage tank and reminding the vaccinator to take away the mist storage tank from a mist storage tank extraction outlet through the human-computer interaction module and guide the vaccinator to complete vaccine inhalation;

Step 6: generating a vaccination record of the vaccine nebulization and saving the vaccination record on the cloud server.

10. The method of use according to claim 9, wherein performing a step 5A after the step 5, wherein the step 5A comprises:

controlling an inhalation quality detection module to detect whether a vaccination process is normally run according to preset vaccination quality requirements; if not, generating notifications for manual intervention or activating preset operations.

11. The method of use according to claim 10, wherein performing a step 5B after the step 5A, wherein the step 5B comprising: controlling a disposable mist storage tank recovery device to open a mist storage tank recovery opening; guiding the vaccinator to put used mist storage tank to the mist storage tank recovery opening by the human-machine interface of the human-computer interaction module; starting medical waste procedures when the mist storage tank is detected being put in the disposable mist storage tank recovery device.

12. The method of use according to claim 9, wherein the step 1 further comprises an automatic recognition and storage procedure comprising: S1: obtaining a vaccine code; S2: retrieving vaccine storage parameters, the nebulization parameters and usage guidelines; S3: detecting whether vaccines are put in the temporary vaccine storage module; S4: starting executing vaccine storage program, and automatically setting storage environment conditions according to the vaccine storage parameters, nebulization parameters and usage guidelines.

13. The method of use according to claim 9, wherein in the step 1, conditions for the determination whether the vaccination is allowed include: whether an age of the vaccinator is within an allowed vaccination range, whether the vaccinator belong to a group who should not get a vaccine, whether the vaccinator belong to a group who should delay vaccination and whether the vaccination record is matched with vaccines disposed in the intelligent vaccine nebulization system; if the vaccination is allowed, entering into the Step 2, otherwise exit.

14. The intelligent vaccine nebulization system according to claim 2, further comprising a disposable mist storage tank recovery device configured to recover and treat medical wastes, and the human-machine interface of the human-computer interaction module is configured to guide the vaccinator to put used mist storage tank to designated recycling place.

15. The intelligent vaccine nebulization system according to claim 4, wherein the dosing transfer module comprises a vaccine information scanner, a pipetting needle, a program-controlled dosing pump and a three-dimensional moving device, wherein the vaccine information scanner is arranged in the vaccine storage chamber, the pipetting needle is connected to the program-controlled dosing pump and the program-controlled dosing pump is provided on the three-dimensional moving device; the program-controlled dosing pump and the three-dimensional moving device are controlled by the intelligent main control module.

16. The intelligent vaccine nebulization system according to claim 2, wherein the mist storage tank comprises a one-way valve, a tank body and a cover; the one-way valve is the portion where the mist storage tank connected to the aerosol output module.

17. The method of use according to claim 10, wherein the step 1 further comprises an automatic recognition and storage procedure comprising: S1: obtaining a vaccine code; S2: retrieving vaccine storage parameters, nebulization parameters and usage guidelines; S3: detecting whether vaccines are put in the temporary vaccine storage module; S4: starting executing vaccine storage program, and automatically setting storage environment conditions according to the vaccine storage parameters, the nebulization parameters and usage guidelines.

18. The method of use according to claim 10, wherein in the step 1, conditions for the determination whether the vaccination is allowed include: whether an age of the vaccinator is within an allowed vaccination range, whether the vaccinator belong to a group who should not get a vaccine, whether the vaccinator belong to a group who should delay vaccination and whether the vaccination record is matched with vaccines disposed in the intelligent vaccine nebulization system; if the vaccination is allowed, entering into the Step 2, otherwise exit.

* * * * *